United States Patent
Kidmose et al.

(10) Patent No.: US 9,408,552 B2
(45) Date of Patent: Aug. 9, 2016

(54) EAR PLUG WITH SURFACE ELECTRODES

(75) Inventors: Preben Kidmose, Maarslet (DK); Michael Ungstrup, Allerod (DK)

(73) Assignee: Widex A/S, Lynge (DK)

( * ) Notice: Subject to any disclaimer, the term of this patent is extended or adjusted under 35 U.S.C. 154(b) by 806 days.

(21) Appl. No.: 13/339,379

(22) Filed: Dec. 29, 2011

(65) Prior Publication Data

US 2012/0209101 A1 Aug. 16, 2012

Related U.S. Application Data

(63) Continuation-in-part of application No. PCT/DK2010/050174, filed on Jul. 1, 2010, and a continuation-in-part of application No. PCT/DK2009/050156, filed on Jul. 2, 2009.

(51) Int. Cl.
| | | |
|---|---|---|
| *A61B 5/0478* | (2006.01) | |
| *A61B 5/00* | (2006.01) | |
| *H04R 25/00* | (2006.01) | |

(52) U.S. Cl.
CPC ............. *A61B 5/0478* (2013.01); *A61B 5/6817* (2013.01); *H04R 25/652* (2013.01); *H04R 25/658* (2013.01); *H04R 2225/77* (2013.01); *Y10T 29/49204* (2015.01)

(58) Field of Classification Search
CPC ............................ A61B 5/6817; A61B 5/6815
USPC .................................. 600/379, 383, 544–545
See application file for complete search history.

(56) References Cited

U.S. PATENT DOCUMENTS

| | | | | |
|---|---|---|---|---|
| 4,601,294 A | * | 7/1986 | Danby et al. ................... | 600/379 |
| 4,741,344 A | | 5/1988 | Danby et al. | |
| 5,673,692 A | * | 10/1997 | Schulze et al. ................. | 600/301 |
| 5,712,917 A | * | 1/1998 | Offutt .................. | H04R 25/606 381/151 |
| 6,556,852 B1 | * | 4/2003 | Schulze ................... | A61B 5/01 600/310 |
| 6,564,106 B2 | * | 5/2003 | Guck et al. ..................... | 607/116 |
| 2003/0045787 A1 | | 3/2003 | Schulze et al. | |
| 2003/0199204 A1 | | 10/2003 | Sauer et al. | |
| 2005/0244024 A1 | | 11/2005 | Fischer et al. | |
| 2006/0094974 A1 | * | 5/2006 | Cain ............................. | 600/544 |
| 2007/0112277 A1 | | 5/2007 | Fischer et al. | |
| 2007/0135717 A1 | * | 6/2007 | Uenishi et al. ................. | 600/485 |

(Continued)

FOREIGN PATENT DOCUMENTS

| | | |
|---|---|---|
| AU | 640068 | 7/1992 |
| CN | 1160205 A | 9/1997 |

(Continued)

OTHER PUBLICATIONS

International Search Report for PCT/DK2009/050156 dated Dec. 7, 2009.

(Continued)

*Primary Examiner* — Lee S Cohen
*Assistant Examiner* — Erin M Cardinal
(74) *Attorney, Agent, or Firm* — Sughrue Mion, PLLC

(57) ABSTRACT

An ear plug (200) comprises a shell (206) with at least two electrodes (201-205) adapted for measuring brain wave signals, said electrodes (201-205) being connected with means for processing the measured signals, wherein the contours of the outer surface of the ear plug (200) and the electrodes (201-205) are individually matched to at least part of the ear canal and the concha of the user. The invention further provides a method for producing an ear plug.

18 Claims, 7 Drawing Sheets

(56) References Cited

U.S. PATENT DOCUMENTS

| | | | |
|---|---|---|---|
| 2008/0249594 A1* | 10/2008 | Dietrich | A61N 1/36014 607/115 |
| 2009/0112071 A1* | 4/2009 | LeBoeuf et al. | 600/301 |
| 2009/0228066 A1 | 9/2009 | Hirata et al. | |
| 2010/0198282 A1* | 8/2010 | Rogers | A61F 7/007 607/3 |
| 2010/0217098 A1* | 8/2010 | Leboeuf et al. | 600/301 |
| 2010/0298667 A1 | 11/2010 | Uenishi et al. | |
| 2012/0177233 A1* | 7/2012 | Kidmose et al. | 381/314 |
| 2012/0316418 A1* | 12/2012 | Kilsgaard et al. | 600/379 |
| 2013/0184552 A1* | 7/2013 | Westermann | A61B 5/0006 600/378 |

FOREIGN PATENT DOCUMENTS

| | | |
|---|---|---|
| DE | 4041105 A1 | 6/1992 |
| EP | 1351551 A1 | 10/2003 |
| EP | 1587343 A2 | 10/2005 |
| EP | 1671578 A1 | 6/2006 |
| JP | 4-208135 A | 7/1992 |
| JP | 11-128174 A | 5/1999 |
| JP | 2007-21106 A | 2/2007 |
| JP | 2007-244572 A | 9/2007 |
| JP | 2009-45368 A | 3/2009 |
| JP | 2009-50368 A | 3/2009 |
| KR | 10-2006-0063962 A | 6/2006 |
| WO | WO 9211737 A1 | 7/1992 |
| WO | WO 03072185 A2 | 9/2003 |
| WO | WO 2006047874 A1 | 5/2006 |
| WO | WO 2007006302 A1 | 1/2007 |
| WO | WO 2007047667 A2 | 4/2007 |
| WO | WO 2008116462 A1 | 10/2008 |

OTHER PUBLICATIONS

International Search Report for PCT/DK2010/050174 dated Sep. 2, 2010.
Office Action for counterpart Chinese Application No. 201080030280.0 dated Sep. 27, 2013, with English translation.
Office Action for corresponding Japanese Application No. 2012-516516 dated May 21, 2013 with English translation.
Office Action for corresponding Korean Application No. 10-2012-7001580 dated Jun. 11, 2013 with English translation.
Japanese Office Action for Japanese Patent Application No. 2012-516516 dated Sep. 3, 2013, with English translation.

* cited by examiner

EAR PLUG WITH SURFACE ELECTRODES

RELATED APPLICATIONS

The present application is a continuation-in-part of application PCT/DK2010/050174, filed on Jul. 1, 2010, in Denmark and published as WO2011000383 A1.

The present application is a continuation-in-part of application PCT/DK/2009/050156, filed on Jul. 2, 2009, in Denmark and published as WO 2011000375 A1.

BACKGROUND OF THE INVENTION

1. Field of the Invention

The present invention relates generally to ear plugs. More specifically, the present invention relates to an ear plug comprising a shell with at least two electrodes adapted for measuring brain wave signals, said electrodes being connected with means for processing the measured signals. The invention further relates to a method of producing an ear plug.

It is generally known, particularly within medical science, to measure brain waves by placing electrodes on the scalp of a subject, whose brain waves it is desired to measure (for simplicity denoted "subject" in the following), and to view, process and interpret the measured brain waves using suitable equipment. Typically, such equipment is an electroencephalograph, by means of which a so-called electroencephalogram (EEG) may be achieved. The EEG is obtained by a measurement and recording of electrical activity in a subject's brain by measuring the electric potential generated on the surface of the subject's scalp by currents flowing between dendrites in the subject's brain. Within medical science EEG's are used for various diagnostic purposes.

2. The Prior Art

A system for such a use is known from WO-A1-2006/047874, which describes measurement of brain waves by use of electrodes placed in connection with at least one of the ears of the subject, i.e. placed on an outer ear part or placed in the ear canal. The measurements are used particularly for detecting the onset of an epileptic seizure. WO-A1-2006/047874 also describes the use of electrodes in pairs as detection and reference electrodes respectively, such a setup being well known in the field of electroencephalography.

Furthermore it is known from WO-A1-2008/116462 to measure the hearing ability of the subject by using a hearing aid to generate a test stimulus signal and transmit said signal to a subject as an acoustic stimulus, and by detecting a brain wave response to said acoustic stimulus signal by use of separate electrodes placed on the subject's scalp and transmitting the brain wave response to an electrophysiological instrument such as an electroencephalograph for processing.

WO-A1-2007/047667 describes an ear plug for measuring EEG-signals. The ear plug comprises an exterior shell with electrodes, the shell being made of a soft, compressible material, such as memory foam, capable of conforming to the interior of an individual's auditory canal. The signals obtained with the ear plug are transmitted to external units for processing and monitoring.

However, at least the signal processing devices of the known systems are, due to their complexity and use of extensive and complicated equipment, confined to use and operation by qualified staff. Furthermore the placement of in by far most cases electrodes and in any case associated wiring on various parts of the subject's scalp and/or head renders the known systems rather unattractive for use outside laboratory surroundings, thus rendering exploitation of the advantages related to the use of brain wave measurements outside the laboratory, e.g in everyday use, rather cumbersome.

With the ear plug according to WO-A1-2007/047667 a solution to the problem regarding the electrodes is proposed. However, several disadvantages remain. There is a risk of insufficient contacting between the ear canal and the electrodes due to the shell, which again may cause poor or insufficient signal quality. Also, the shell properties imply a low durability of the proposed ear plug. Furthermore, it is well known, that ear plugs of the type proposed in WO-A1-2007/047667 cause an enlarged risk of the user suffering from occlusion and/or insufficient ventilation of the ear canal, particularly during long term use.

SUMMARY OF THE INVENTION

The present invention therefore aims at providing an ear plug by means of which ear plug electrical brain wave measurements such as EEGs become possible without or with a minimum of use of extensive and complicated equipment, which ear plug may be used in an uncomplicated way in everyday life while obtaining high quality brain wave signals, and with which the advantages related to the use of brain wave measurements may be readily utilized outside the laboratory.

The invention in a first aspect provides an ear plug comprising a shell with at least two electrodes adapted for measuring brain wave signals, said electrodes being connected with means for processing the measured signals, wherein in that the contours of the outer surface of the ear plug are individually matched to at least part of the ear canal and the concha of the user, and wherein the ear plug is made of a dimensionally stable material for identical positioning in the ear canal each time it is inserted.

This ear plug obtains an improved contact between the user's ear canal and the electrodes and a very high degree of repeatability in the placement of the electrodes between individual measurement sessions, in that the ear plug due to being individually matched will be positioned identically in the ear canal each time it is inserted. Thereby measurement uncertainties related to quantitative and qualitative variations due to changed electrode positions or insufficient contact may substantially be avoided.

As the ear plug according to the invention is individually matched, it comprises surface convexities matching the concavities of the specific ear canal of the specific user to whom the plug is individually matched. This has several advantages. Firstly, there is one correct position of the ear plug in the user's ear canal only, and thus the ear plug is easy to insert, and it is easy to determine when it is in its correct position. Secondly, the right and left ear plugs cannot be confused as each ear plug matches one specific ear canal. Furthermore, the ear plug according to the invention is firmly secured in the ear canal of the user substantially by friction alone, and produces no static pressure against the skin of the ear canal. Consequently, the ear plug according to the invention is very well suited for long term use, e.g. for use during the night, as the long term inconveniences caused by the static pressure against the skin of the ear canal in conventional ear plugs are eliminated. Also, the ear plug according to the invention is very well suited for use by children and other persons who cannot insert the plug into their ear canal themselves, as the plug is very easy to insert and as it is easy for an assisting person to determine when the plug is in proper place. Also, the ear plug according to the invention will not fall out of the ear canal during physical activity.

Individually matched ear plugs are widely known and used within the hearing aid industry as a completely-in-canal (CIC) hearing aid, an in-the-ear (ITE) hearing aid, or as the ear plug of a behind the ear (BTE) hearing aid. For instance WO-A1-92/11737 describes a technology for preparing such ear plugs by tracing the shape of a users outer ear, and particularly of a users ear canal and concha, converting the traced shape to a digital form such as a three-dimensional computer model, optimizing the shape of the ear plug based on the three-dimensional computer model and finally building the ear plug based on the optimized computer model by means of a computer controlled production process, such as laser printing. Furthermore, the use of a dimensionally stable material provides for a significantly improved durability, as well as for avoiding occlusion and improving ventilation of the user's ear canal during use of the ear plug, as such a material offers the possibility to have a ventilation duct of optimal size while maintaining a good skin connection. However, WO-A1-92/11737 is not concerned with electrodes of any kind.

Providing the at least two electrodes with a shape following the local contours of said shell at the electrode and thereby being individually matched to the concha and the ear canal of the user has the advantage of providing smooth transitions between the electrode and the surrounding part of the shell of the ear plug, and particularly a generally smooth shell surface, which increases the wearing comfort of the user.

Another advantage related to an ear plug according to the invention is the provision of the possibility of placing electrodes for measuring brain waves in a position deep within the ear canal of the user. Thereby artifacts due to muscle activity may be reduced or eliminated, because the plug will always be placed in the same way and have tight connection with the skin as there are no muscles in the human auditory canal and thereby no movement of the plug inside the canal or in the concha.

Furthermore, an ear plug according to the invention provides for that a subject's brain waves may be monitored and measured, and that the brain waves measured may be transmitted to other internal or external electronic components or units for further processing. With such an ear plug, it is possible to measure brain waves and transmit the measured brain waves to electronics for processing the measured brain waves using a simple and small device that is inconspicuous when worn by the user and thus more attractive to wear outside the laboratory. Also such an ear plug provides for the possibility of using the brain wave measurements in mobile equipment as it is considerably more practical to wear and use outside the laboratory as compared with the prior known devices.

Enabling the measurement of brain waves during everyday life by using an ear plug according to the invention provides the main advantage of enabling continuous around the clock monitoring of various factors relating to the user's health state, such as heart rate, temperature, blood sugar level, state and/or seizure onsets related to various diseases etc., in a way interfering as little as possible in the user's everyday life both on a practical and aesthetic level. An example of such a use of brain wave measurements, namely to detect onsets of epileptic seizures, is as mentioned above described in WO-A1-2006/047874.

In a preferred embodiment, the ear plug according to the invention is an ear plug adapted for use in a hearing aid, but it may in principle be any type of ear plug, thereby enabling persons not needing hearing aids to likewise benefit from the advantages of the invention.

Enabling the measurement of brain waves during everyday life by using an ear plug according to the invention in a hearing aid has a variety of uses and advantages. Such uses and advantages include, but are not limited to:

a) On insertion of the hearing aid in the ear canal of a user, determining whether the hearing aid plug is placed correctly, i.e. whether the plug is in contact with the tissue of the ear canal. If one or more electrodes are not in (proper) contact with tissue, the measured signal will be weaker than when all electrodes are properly contacting the tissue. If no electrodes are in contact with tissue, the hearing aid will automatically switch to stand-by.

b) Automatically informing the user, e.g. with a designated signal, if the hearing aid is not placed correctly in the ear canal or is malfunctioning.

c) Detecting conditions or events related to the user or to the surroundings by combining the signal detected by means of the electrodes with signals obtained with other types of sensors such as microphones, accelerometers, infrared sensors etc. Such a combined use of different sensor types has the purpose of gaining better information than would be possible using one sensor type alone, and is a principle generally known as sensor fusion.

According to a preferred embodiment, the ear plug is made of a dimensionally stable material, whereby an improved repeatability in the positioning of the electrodes may be achieved.

The term "dimensionally stable material" is as used herein intended to mean materials that once shaped into a device having a particular shape substantially maintain that shape and stay resilient over a long period of time and during repeated use of the device.

Furthermore, particularly preferred dimensionally stable and resilient materials likewise comprise a certain amount of flexibility to provide for an ear plug being comfortable to wear within the ear canal, such as to minimize irritation.

According to a preferred embodiment, the electrodes are individually matched to at least part of the ear canal and the concha of the user, whereby a further improved fit of the ear plug in the ear canal of the user may be achieved.

According to a preferred embodiment, the means for processing electrical signals is adapted for delivering a signal to the user. Such a signal may in principle be any type of signal, such as a tactile or visual signal but is preferably either an audible signal aimed directly at the user, or a signal transmitted to an external unit in order to gain the user's attention. Thereby the possibility of direct surveillance of the user's health state is provided, and an action may be taken immediately upon detecting, preferably by means of said means for processing electrical signals, that the user's health state is developing in an undesired way. For instance possible actions that may be taken by the means for taking an action include, but are not limited to, issuing a warning such as an acoustic, visual or tactile signal, drawing the user's attention to his or her health state, or transmitting relevant user health data to a monitoring unit to enable e.g. the user or other relevant persons to take an appropriate action, such as medication of the user.

According to another preferred embodiment, the means for processing electrical signals is external means whereby another version of a particularly simple ear plug is provided by minimizing the quantity of electronics to be accommodated in the ear plug. The means for processing may also include transmission of the electrical signals.

According to a particularly preferred embodiment, the means for processing electrical signals is located in the ear plug, whereby a particularly simple ear plug with a minimum of externally placed equipment is provided, which ear plug is particularly convenient for mobile use during everyday life.

According to a preferred embodiment, the connecting means comprise conductive wiring drawn in or through the shell and/or on the surface of the shell of the ear plug, whereby the connecting means are provided in a particularly simple manner with the particular advantage of avoiding connecting means being placed on the outside of the shell of the ear plug.

According to a preferred embodiment, the conductive wiring drawn on the surface of said shell is arranged to form, or may be adapted to accommodate, at least one of said electrodes, whereby the electrodes may be formed in a particularly simple manner.

According to a preferred embodiment, the ear plug further comprises a pin or a rivet extending between the electrode and the connecting means, through at least a part of the shell of the ear plug in such a way that a part, such as a head, of the pin or rivet is arranged flush with or on the surface of the shell. Thereby the part of the connecting means extending through at least part of the shell of the ear plug is provided as a more stable and durable connection, particularly being less prone to loose connections due to wear induced stresses and strains.

According to a further embodiment, the part, e.g. the head, of said pin or rivet, arranged flush with or on said surface of said shell is adapted to form or accommodate said at least one electrode, whereby the electrical connection between the pin or rivet and the electrode is established automatically and is of increased durability.

According to a preferred embodiment, the ear plug comprises at least one recess in which the at least one electrode is mounted, the bottom surface of the recess following the contours of the outer surface of the ear plug, whereby the contours of the electrode mounted in the recess will take shape after the contours of the recess and thereby the ear plug. Preferably, the electrode is made of an electrically conductive flexible material, preferably an electrically conductive silicone.

According to a preferred embodiment, the electrode is held in the recess by the electrode comprising at least one of a close fit to the recess, at least one convexity corresponding to at least one concavity provided in the recess and an adhesive, thereby ensuring a well secured electrode, that is simultaneously easy to exchange when worn down.

According to a preferred embodiment, the electrodes are polarizable electrodes, preferably made of an alloy, e.g. stainless steel or platinum-iridium, or a noble metal, e.g. silver, titanium, platinum or tungsten, such materials providing for electrodes being particularly durable when exposed to the conditions prevailing in the human ear canal.

According to another preferred embodiment, the electrodes are non-polarizable electrodes, preferably Ag/AgCl electrodes, which enables the use of electrodes of a very small size, such as e.g. 1 mm$^2$.

According to a preferred embodiment, the at least two electrodes comprise an area of at least 1 mm$^2$, preferably between 1 mm$^2$ and 30 mm$^2$, as such a size of electrodes has proven to be a particularly good compromise between size and signal quality, particularly signal strength. More specifically, electrodes of such a size have been shown to be large enough to enable provision of signals of sufficient strength and thus quality for the further processing.

Furthermore, as larger electrodes provide signals of better quality, and as a general standard electrode size is in the order of 1 cm$^2$, the mentioned preferred interval is also chosen as a compromise between electrode size and obtaining sufficient separation between the individual electrodes. Sufficient separation between electrodes is of great importance to ensure that the signals obtained by two neighbouring electrodes are not mutually affected; either through the electrodes or through the tissue area on which the electrodes are placed.

The at least two electrodes are provided to the shell of the ear plug by means of a technique chosen from the group consisting of Physical Vapour Deposition (PVD), sputtering, a printing technique such as pad-printing and an inkjet technique using conductive ink. These methods are preferred, as they are methods proven to be particularly useful and efficient for placing a metallic material on a surface, here being the shell of an ear plug.

An alternative method for providing a surface with a metallic layer is known from EP-B1-1587343 describing how to provide a behind-the-ear component of a hearing aid with a high frequency antenna or a coil for transmitting electromagnetic energy or data.

Another alternative method is described in EP-B1-1351551 and is known as MID (Moulded Interconnect Device) moulding. In MID moulding the moulding material, such as a plastic, is provided with metallic beads, such as Silver-Palladium (Ag—Pa). When a structure has been moulded, the Ag—Pa beads may be activated, e.g. by laser. When subsequently providing a metallic layer to the surface of the structure, the metallic layer will be confined to the activated areas, and the activated areas may furthermore be used as conductors for transmitting an electrical signal from the metallic layer.

The invention, in a second aspect, provides a system comprising an ear plug, the ear plug being individually matched to at least part of the ear canal and the concha of the user and made of a dimensionally stable material, the ear plug having at least one electrode for measuring brain wave signals and a behind-the-ear (BTE) component, where the BTE component accommodates said means for processing the brain wave signals.

According to a preferred embodiment, the BTE component comprises at least one electrode for measuring brain wave signals.

Preferably, the ear plug of the system is an ear plug according to any one embodiment of the first aspect of the invention.

The invention, in a third aspect, provides a method of producing an ear plug with surface electrodes for measuring brain wave signals comprising the steps of, tracing the shape of a part of the user's ear canal and concha, converting the traced shape into a digital form such as a three dimensional computer model and building the ear plug based on the computer model by means of a computer controlled production process.

According to a further preferred embodiment the at least one electrode is placed individually according to the shape of the user's outer ear.

A further aspect of a method according to the invention includes producing an ear plug as described above, preferably using Stereolithography (SLA), Selective Laser Sintering (SLS), Fused Deposition Modelling (FDM) or similar printing techniques, the method comprising the steps of providing a shell provided with a surface having contours being individually matched to the contours of the ear canal of a user, the shell being comprised of a dimensionally stable material, and comprising the further step of providing on and/or in a surface of said shell at least two electrodes adapted for detecting electrical signals such as brain waves.

Another further aspect of a method according to the invention includes one or more of the further steps of:
  providing connecting means connecting the at least two electrodes with means for processing electrical signals;
  providing each of the at least two electrodes with a shape following the local contours of the shell at the electrode; and providing the ear plug with means for processing electrical signals and/or means for taking an action in response to an output of said means for processing electrical signals.

In a further aspect of a method according to the invention the step of providing said connecting means comprises providing conductive wiring drawn in and/or through said shell of said ear plug and/or comprises providing a pin or a rivet extending through at least a part of said shell of said ear plug in such a way that a part, such as a head, of said pin or rivet is arranged flush with or on said surface of said shell.

In another further aspect of a method according to the invention includes that the step of providing said at least two electrodes is performed by means of a technique chosen form the group consisting of Physical Vapour Deposition (PVD), sputtering, a printing technique such as pad-printing and an inkjet technique using conductive ink.

BRIEF DESCRIPTION OF THE DRAWINGS

The invention will now be described in further detail based on a non-limiting exemplary embodiment, and with reference to the drawings. In the drawings.

DETAILED DESCRIPTION OF THE INVENTION

Figure 1:
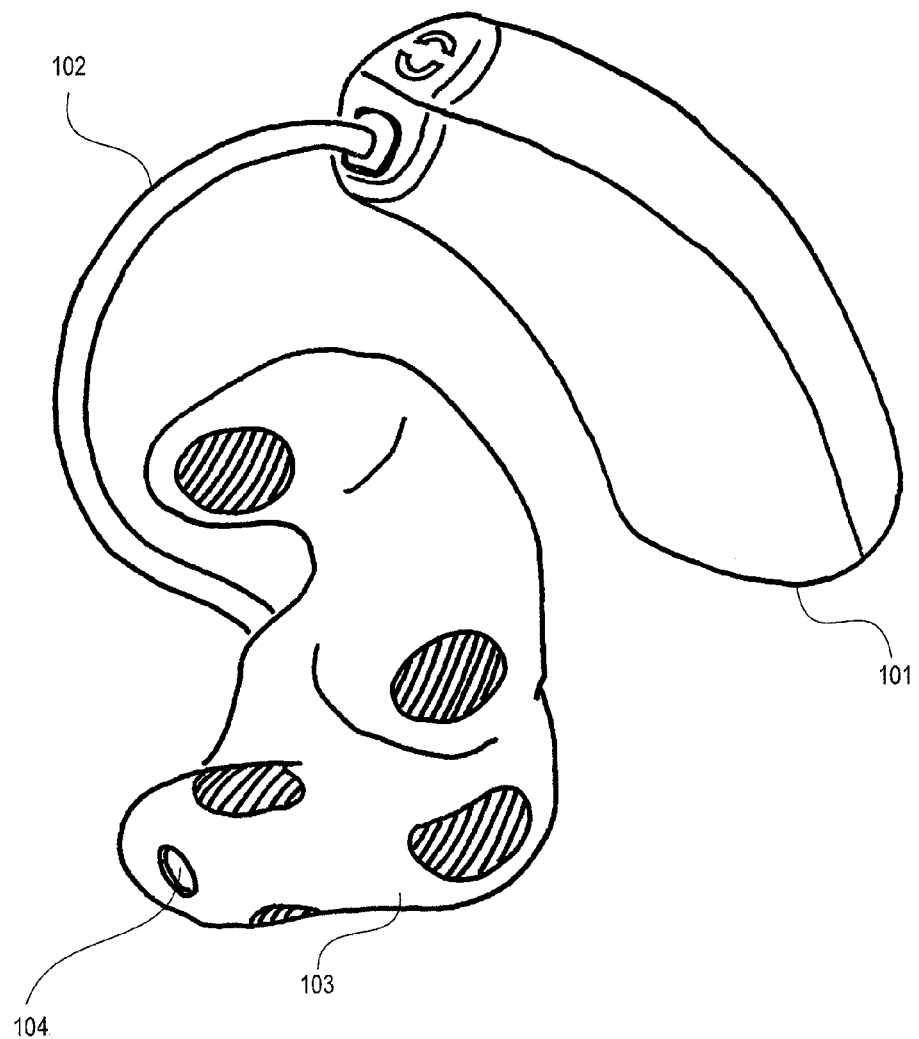
FIG. 1 illustrates the system of an ear plug together with a BTE component

FIG. 1 shows an example of an ear plug according to the invention in a system with a behind-the-ear (BTE) component. The system comprises a BTE-component 101, an ear plug 103 according to the invention for insertion in the ear canal of a user, the ear plug 103 thus constituting an in-the-ear (ITE) component, and a connection means 102 for connecting the BTE-component 101 and the ear plug 103. The ear plug 103 comprises a surface and a connection opening 104. In one embodiment of the invention, this system could be a hearing aid.

The opening 104 is in one embodiment of the system an opening for a receiver of a hearing aid. The receiver is placed in an ear plug 103 in a so called receiver-in-the-ear (RITE) solution, connected to the BTE-component 101 through connecting means 102. In a variant the hearing aid receiver is be placed in the BTE-component and sound is transmitted to the user through connection 104 connected to the BTE-component via a sound tube 102. The connection opening 104 may also act as a ventilation duct to ensure good ventilation of the ear canal.

In another embodiment the system is adapted to monitor the medical state of the user. The brain wave signals detected by the electrodes are transmitted to the BTE-component for further processing. Here the opening 104 may be used to signal the user in case of a seizure by placing a receiver either in the plug 103 or in the BTE-component 101. The opening 104 may also be a ventilation duct.

Figure 2:
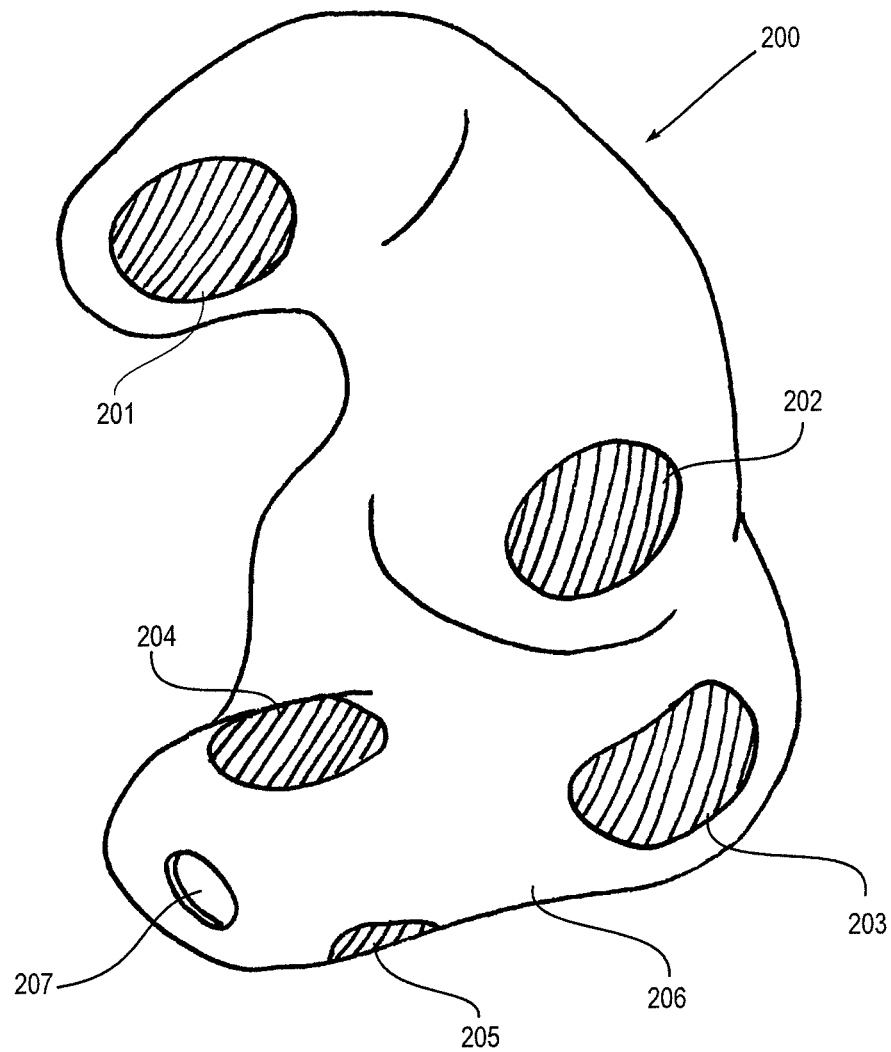
FIG. 2 illustrates an ear plug according to an embodiment of the invention.

FIG. 2 shows an ear plug 200 according to the invention. The ear plug 200 comprises a shell 206 and five electrodes 201, 202, 203, 204 and 205 adapted for detecting electrical signals such as brain waves. The ear plug 200 further comprises an opening 207 connecting the ear canal of the user with the surroundings thus avoiding occlusion, i.e obstructing the hearing of the user.

The surface of the shell 206 of the ear plug 200 comprises a double curvature and is provided with contours being individually matched to the contours of the ear canal of a user. As mentioned, such a shell 206 may be produced for instance using the technology described in the WO-A1-92/11737, or any other suitable technology. The geometry of the ear of a user may for instance be replicated by making a wax impression of the ear and, subsequently, performing a three-dimensional scanning of the wax impression. Alternatively a direct measurement of the ear using an ear scanner may be performed. Subsequently the obtained three-dimensional model of the ear is used as a basis for modelling a three-dimensional model of the ear plug using suitable software. The actual ear plug is then produced based on the three-dimensional model by using a suitable method. Typically such a method is a rapid prototyping method, such methods being generally known within the field of hearing aids. Examples of rapid prototyping methods are Stereolithography (SLA), Selective Laser Sintering (SLS) and Fused Deposition Modelling (FDM). The shell 206 of the ear plug is produced of a dimensionally stable and resilient material capable of maintaining a particular shape over a long period of time and during repeated use of the ear plug, while preferably also comprising sufficient flexibility to provide an ear plug being comfortable to wear within the ear canal, particularly during extended continuous use. Typical materials for producing an ear plug, and particularly a shell of an ear plug, according to the invention include, but are not limited to, plastic materials and silicones.

The electrodes 201-205 are arranged or integrated on the surface of the shell 206 of the ear plug 200. The electrodes 201-205 are each adapted to follow the respective local contours of the shell 206 in the close vicinity of the electrode 201-205. Preferably, the electrodes protrude slightly from the surface of the shell of the ear plug, thereby providing for electrodes pressing more tightly against the skin than the surface of the shell, and thus for improved electrical contact between the skin of the user and the electrodes. Alternatively the electrodes 201-205 may be embedded or integrated in the surface of the shell 206 of the ear plug 200, or the surface of the electrodes 201-205 may be flush with the surface of the shell 206.

The exact number of electrodes 201-205 provided may be more or less than the five electrodes 201-205 shown and remain uncritical. However, as the actual detection of brain waves is preferably performed with respect to a reference point, the provision of at least two electrodes is preferred, as such a configuration provides for the possibility of allowing at least one of the electrodes to act as reference point, thus being a reference electrode, for the remaining electrodes, thus being detecting electrodes, thereby improving the quality of the measured signals. Alternatively the electrodes 201-205 may be set up to operate in clusters, e.g. in pairs, with one electrode acting as a reference electrode for one or more other electrodes, thus acting as detecting electrode(s).

The electrodes 201-205 may be polarizable electrodes or non-polarizable electrodes. Polarizable electrodes are electrodes transferring a potential capacitively, i.e. with little or without any transport of charges from the skin to the electrode. Non-polarizable electrodes are electrodes by which a transport of charges between the skin and the electrode is conducted with little or without loss of energy in the transition between skin and electrode. In such electrodes a transformation occurs in the transition from ion transport in the skin to electron transport in the electrode, whereby a current is running in the transition.

In case of polarizable electrodes, the electrodes 201-205 are preferably made of alloys such as stainless steel and platinum-iridium and noble metals such as silver, titanium, platinum and tungsten. In principle, however, any material suitable for resisting the harsh environment in the ear canal of a human may be used.

In case of non-polarizable electrodes, the electrodes 201-205 are preferably made of silver-silver chloride (Ag/AgCl). Ag/AgCl electrodes may be made by means of a sintering process, in which a die is filled with a mixture of powdered Ag and AgCl and compressed in a press to form a pellet. The pellet is then removed from the die and baked at 400° C. for a suitable amount of time, normally several hours. The resulting sintered electrode has a high durability, and is a preferred type of electrode for use in the embodiments shown on FIGS. 4A, 4B and 5B and described below.

Alternatively, Ag/AgCl electrodes may be made by chlorination performed by electrolysis in hydrochloric acid in a concentration with a pH of 2, in which a reference electrode made of silver is used. The electrodes to be chlorinated are likewise made of silver. A difference in potential of about 1 V between reference electrode and electrodes to be chlorinated is used, and the electrodes to be chlorinated are subjected to a constant current of 5 to 6 mA/cm$^2$ for a duration of between 60 and 100 seconds at a temperature of 20° C. The magnitude of the current depends on the size of the electrodes to be chlorinated—the smaller the electrode the smaller the current needed. Preferably the electrodes to be chlorinated are degreased and rinsed off prior to chlorination.

On one hand, in order to provide signals of sufficient quality and strength the electrodes 201-205 should each be provided with a suitably large surface area. On the other hand, the electrodes 201-205 should not be larger than strictly necessary to have as big a distance between the electrodes as possible in order to measure the potential difference between the electrodes. A suitable electrode size or electrode surface area has, for polarizable electrodes, been shown to be at least 10 mm$^2$, with a preferred size interval being 10 to 30 mm$^2$, while non-polarizable electrodes may be made much smaller, e.g. as small as 1 mm$^2$.

As another alternative the ear plug 200 may also be provided with sensors of another type than electrodes 201-205 adapted for detecting brain waves, thereby e.g. providing for the possibility of so-called sensor fusion as mentioned above.

In order to further improve the quality of the signals detected by means of the electrodes 201-205, the ear plug 200 may comprise a conductive gel (not shown) in connection with the electrodes 201-205, or a conductive gel may be applied to the ear plug 200 in connection with the electrodes 201-205.

Figure 3:
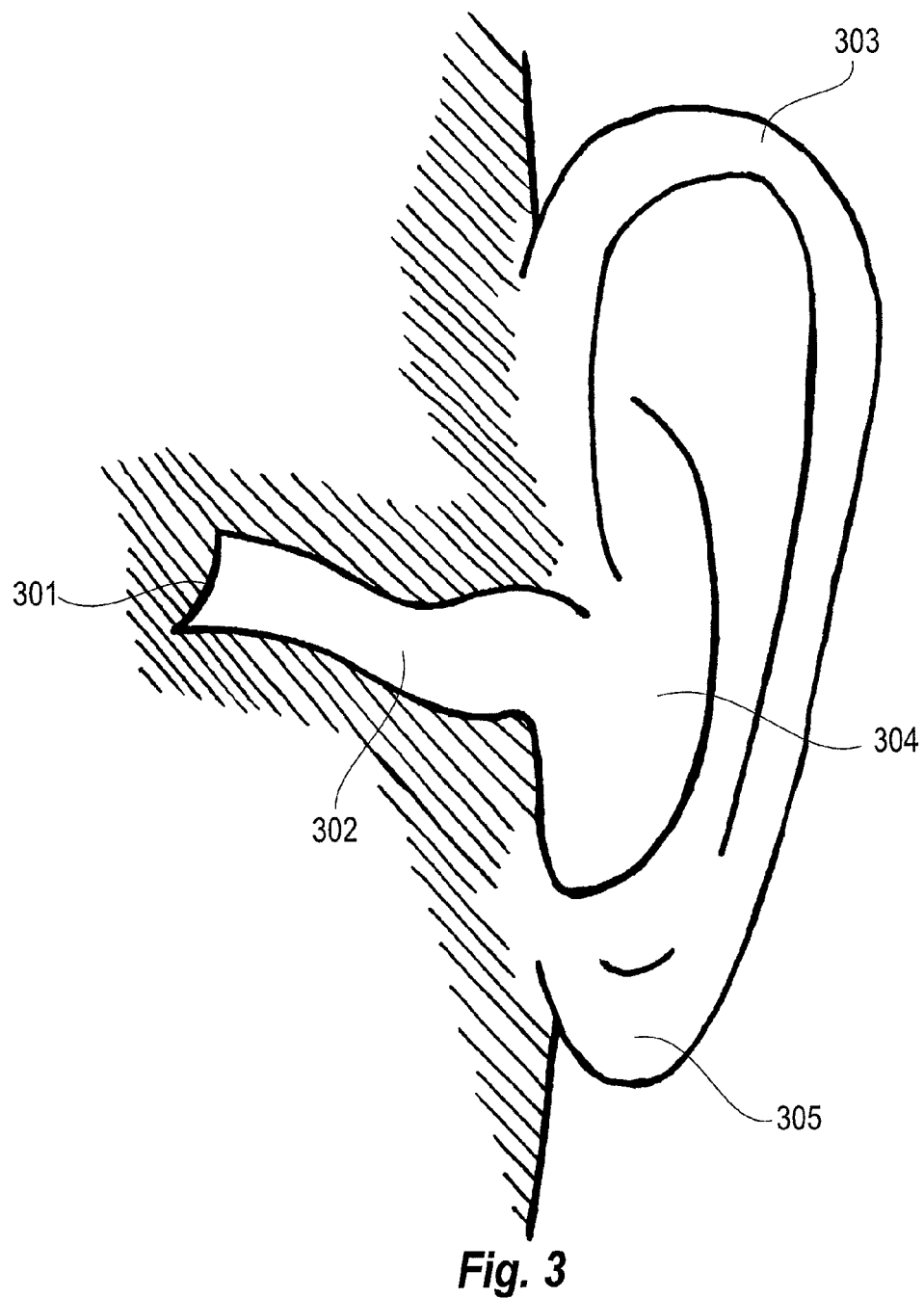
FIG. 3 illustrates a cross section of the outer ear of the human ear.

FIG. 3 shows a cross sectional view of the outer ear. Generally a human ear comprises an eardrum or tympanic membrane 301, an ear canal or auditory canal 302, a helix 303, an concha 304 and an earlobe 305.

As mentioned, the surface of the shell 206 of the ear plug 200 is provided with contours being individually matched to the contours of the ear canal of a user. Particularly the contours of the shell 206 of the ear plug 200 are individually matched to the external part 302 of the ear canal and to the concha 304, such that when a user inserts his or her ear plug 200 into the external part 302 of the ear canal, the electrodes 201-205 lie in physical contact with the skin of the external part 302 of the ear canal and/or the concha 304 and following the contours of the external part 302 of the ear canal and the concha 304, through which brain waves may then be measured.

Figure 4A:
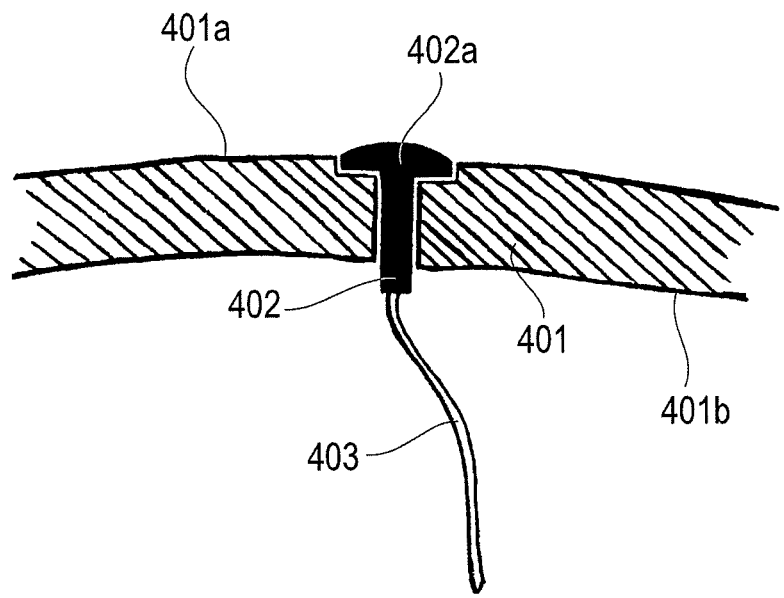
FIG. 4A shows a cross sectional view of a first embodiment of an electrode and connecting means of an ear plug according to an embodiment of the invention.
Figure 4B:
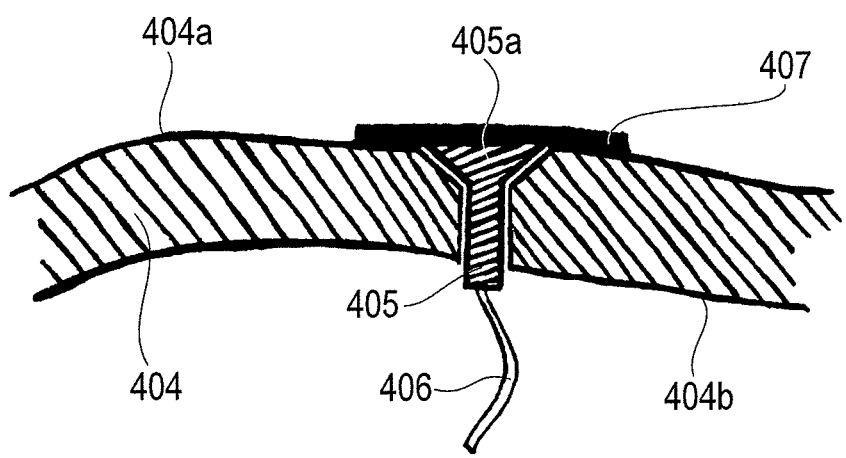
FIG. 4B shows a cross sectional view of a second embodiment of an electrode and connecting means of an ear plug according to an embodiment of the invention.

With reference to FIGS. 4A and 4B, showing different embodiments of an electrode and connecting means of an ear plug according to the invention, suitable methods for integrating electrodes in an ear plug according to the invention shall be described in the following.

FIG. 4A shows a cross sectional view of a shell 401 of an ear plug through which a rivet 402 has been inserted such that the head 402a of the rivet 402 is placed in a corresponding recess in the shell 401 with a surface protruding slightly from the outer surface 401a of the shell 401. In this case the head 402a of the rivet 402 is adapted such as to form the electrode adapted for measuring brain waves. Alternatively a separate electrode may be produced on or in, e.g. in a recess in, the head 402a of the rivet 402. In principle any type of suitable conductive element, such as e.g. a pin, may be used in place of the rivet 402.

At an end of the rivet 402 protruding through—or, if the rivet 402 alternatively extends only partially through the shell 401, the end of the rivet 402 being nearest to—the inner surface 401b of the shell 401 a connecting means 403 is attached. Alternatively the rivet 402 and the connecting means 403 may be one integral unit.

The connecting means 403 is an electrical connecting means connecting the electrode with electronic components embedded in the interior of the ear plug and/or to a connecting means for connecting the ear plug with other external units.

FIG. 4B shows a cross sectional view of another embodiment of a shell 404 of an ear plug through which a rivet 405 has been inserted such that the head 405a of the rivet 405 is placed in a corresponding undercut in the shell 404 with a surface, preferably and as shown a surface of the head 405a, of the rivet 405 being flush with, or alternatively lowered slightly below, the outer surface 404a of the shell 404. An electrode 407 is placed on the outer surface 404a of the shell 404 such that it follows the contour of the shell and covers the surface of the head 405a of the rivet 405 at least partially but preferably and as shown completely. Alternatively the electrode 407 may also be placed in a undercut such that its outer surface is flush with, or lowered slightly below, the outer surface 404a of the shell 404. Possible methods for producing such an electrode include, but are not limited to, Physical Vapour Deposition (PVD), sputtering, a printing method such as pad-printing, and an inkjet technique using conductive ink.

The rivet 405 protrudes through the thickness of the shell 404, and is at its end protruding from the inner surface 404b of the shell 404 connected to connecting means 406 serving the same purpose as the connecting means 403 described in connection with FIG. 4A.

Figure 5A:
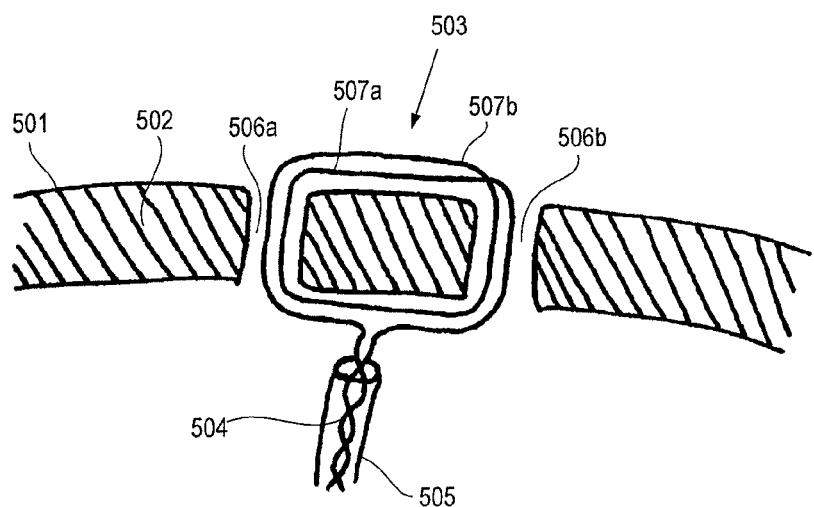
FIG. 5A shows a cross sectional view of a third embodiment of an electrode and connecting means of an ear plug according to an embodiment of the invention.

Referring to FIG. 5A, an alternative to using a rivet 405 is to provide the shell 502 with at least one hole, in the embodiment shown two holes 506a, 506b, suitable for threading a connecting means 503 through the shell 502. In the embodiment shown the connecting means 503 is one wire threaded through the holes 506a and 506b to form two loops 507a and 507b. The two ends of the wire are twisted and shielded by 505, each end of the wire being connected to an analog front end. This analog front-end is a processor for processing or transmitting the signal. However another number of conducting wires, e.g. two, three or four, is likewise possible. In the embodiment shown, the part of the wire 503 situated on the outer surface 501 of the shell 502 is adapted to form the electrode. In this connection the use of a wire as shown in FIG. 5A has been shown to create a sufficient amount of contact to form an electrode. Also, different types, e.g. having different cross sectional configurations, of wire may be used. For instance, in case of a part of the wires forming an electrode, the use of a wire having a flat cross section may improve the amount of contact. The wire 503 may also act as a base for attaching an electrode to the ear plug. The twisted pair of wires 504 going to and from 503 is for protection enclosed in an isolating material 505. Irrespective of the method used each electrode provided on the shell of the ear plug should be connected to a connecting means for transferring the measured signals for further processing.

Figure 5B:
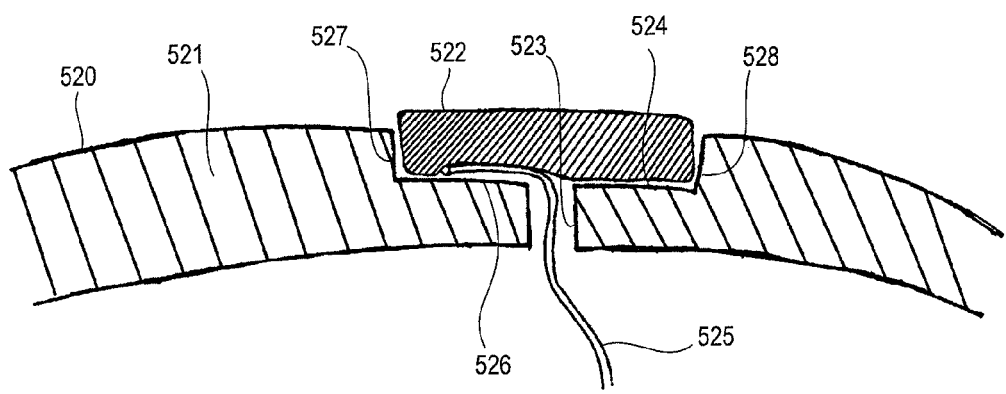
FIG. 5B shows a cross sectional view of a fourth embodiment of an electrode and connecting means of an ear plug according to an embodiment of the invention.

FIG. 5B shows another alternative embodiment of an electrode 522 provided in the shell 521 of an individually matched ear plug 520 according to the invention. The shell 521 of the ear plug 520 is provided with a recess 524 having a bottom surface 526 with a contour following the double curvature of the ear plug 520. The circumference of the recess 524 may have any suitable shape such as e.g. circular or rectangular. An electrode 522 made of an electrically conductive flexible material is mounted in the recess 524. The electrically conductive flexible material may e.g. be an electrically conductive silicone. The thickness of the electrode 522 is preferably equal to or slightly larger than the depth of the recess 524. Thereby, and due to the surface contour of the bottom surface 526 of the recess 524, the electrode 522 is caused to follow the same double curvature as the individually matched ear plug 520, and thus the surface of the ear canal of the user.

The electrode 522 is held firmly in place in the recess 524 by friction by being provided with a close fit to the recess 524. Alternatively, or in addition, the electrode 522 is held firmly in place in the recess 524 by being provided with an adhesive or by the recess 524, preferably one of the side surfaces 527, 528 of the recess 524, being provided with a suitable concave shape (not shown) into which the flexible material of the electrode 522 and/or corresponding convexities (not shown) provided on the electrode 522 is forced when inserted into the recess 524. The electrode 522 may be an exchangeable part. For purposes of electrical connection of the electrode 522, the recess 524 is provided with a hole 523 extending towards the inside of the ear plug 520, through which hole 523 an electrical conductor 525 is passed and connected to the electrode 522.

The electronic components embedded in the interior of the ear plug may comprise, but are not limited to, such components as measurement electronics, analog digital converters, means for taking an action in response to an output of another electronic component, batteries, microphones and threaded or wireless connecting means for connecting the ear plug to external units and other signal processing means. Such an external unit may by way of example be a preferably portable, surveillance unit for monitoring a medical condition of the user. The external unit may, in embodiments in which at least some of the electronic components are not embedded in the ear plug, comprise one or more, and in a preferred embodiment all, of the electronic components otherwise located within the ear plug. The phrase "means for processing the measured signals" is where used intended to be a general term encompassing all of the electronic components that are either embedded in the ear plug or located in an external unit.

Figure 6:
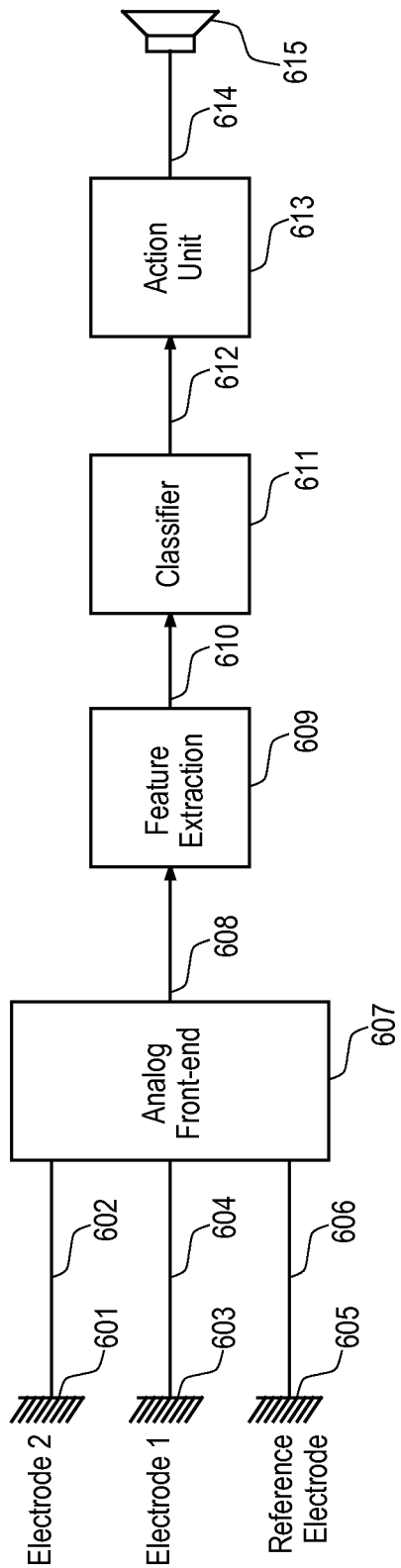
FIG. 6 is a diagram showing an embodiment of the electronics of an ear plug according to an embodiment of the invention.

FIG. 6 shows an example of an ear plug in a monitoring device illustrating a preferred example of electronic components for processing the measured data accommodated in the interior of an ear plug. The electrodes 601, 603 and the reference electrode 605 are by means of respective connection means 602, 604, 606 connected to an analog front-end 607, which preferably comprises an amplifier and an analog-digital converter. The output 608 of the analog front-end 607 is transmitted to the feature extraction unit 609. The feature extraction unit 609 may be regarded as a dimension reduction unit as it reduces the number of dimensions of a vector from a higher number to a lower number of dimensions by analysing which vectors in the signal can represent the overall signal, while maintaining the relevant information carried by the signal. In other words the feature extraction unit could broadly be understood as a data filter.

Data from the feature extraction unit 609 are transmitted via 610 to the classifier 611. The classifier 611 should be understood as the unit that determines what information can be extracted from the measured brain wave signal. The classifier 611 is a trained unit. The classifier 611 is trained to interpret how the individual responds to each situation or medical condition. For instance signals at 7, 8 and 9 Hz may be grouped together whereas a signal at 11 Hz will be grouped with a group of higher frequency signals.

The action unit 613, receiving an output of the classifier 611 via 612, can by way of a non-limiting example be described as a statistic filter, which has a threshold limit of when to take an action according to the measured brain wave signal. The action unit 613 integrates the measured number of signals outputted by the classifier 611 to ensure that an action will not be taken to inform the user of a medical condition in case of just one sample of signals indicating so. If the classifier 611 is a so-called hard classifier the signals outputted via 612 are binary and reveal whether the signals belong to a given class. If the classifier 611 is a so-called soft classifier the signals outputted via 612 are continuous describing the probability that the signals belong to a given class. It has to be a number of samples indicating the situation within a set timeframe before the action unit will send out a warning. In FIG. 6 this warning will be an audio signal transmitted via 614 and the receiver 615, but the warning signal may also be a visual or tactile message, or it may be a data transmission to an external unit.

Figure 7:
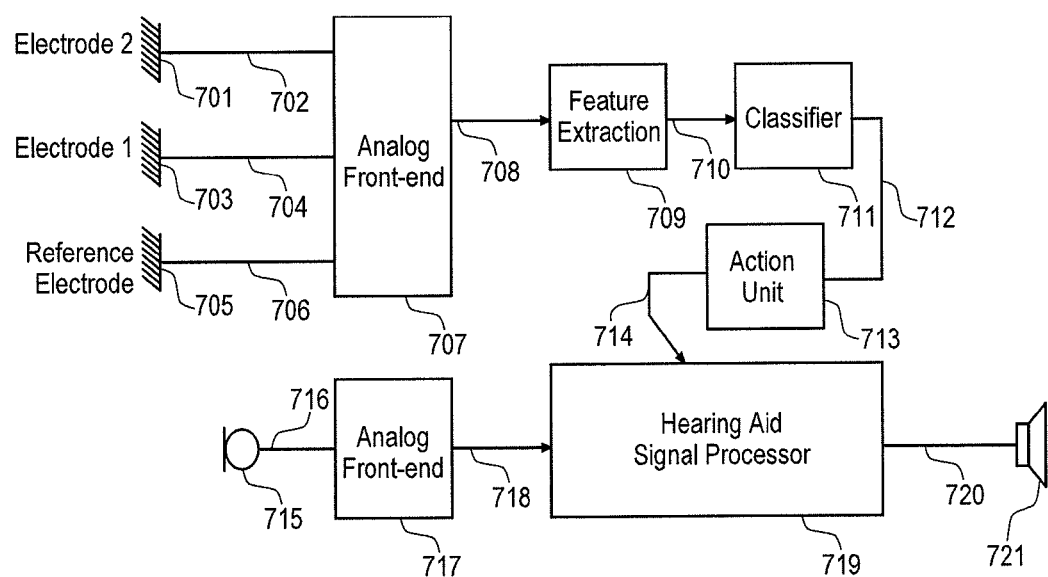
FIG. 7 illustrates an embodiment of the ear plug in a monitoring device.

FIG. 7 shows the electronic components of FIG. 6 in an embodiment with a hearing aid, with elements 701-714 corresponding in structure and function to corresponding elements 601-614 in FIG. 6. The hearing aid illustrated in FIG. 7 includes a microphone 715 connected via line 716 to an analog front end 717 whose output is connected via line connected via line 718 to hearing aid signal processor 719. The processed output of the signal processor 719 is supplied via line 720 to a receiver 721. Here the action unit 713 will send a signal to the hearing aid processor 719 which will then take an appropriate action based on the measured brain wave signal. The hearing aid processor 719 may signal the user in order to warn the user of a medical event. This signal would most likely be an audio signal but could also be visual or a data transmission to an external device. Or the hearing aid processor 719 may adjust the parameters of the hearing aid or switch to another program in the hearing aid, in order to ensure the most suitable adjustment of the hearing aid to the specific situation.

Finally, it should be noted that the above description of preferred embodiments is merely an example, and that the skilled person would know that numerous variations are possible without departing from the scope of the claims.

We claim:

1. An ear plug comprising a shell with at least two electrodes adapted for measuring brain wave signals, said electrodes being connected via a connector to a processor for processing the measured signals, wherein:
   contours of an outer surface of the ear plug are configured to individually match at least part of at least one of an ear canal and concha of a specific user such that said outer surface contours are configured to follow contours of said matched part,
   the electrodes are configured to individually match said part such that a surface of each of said two electrodes to contact the concha or ear canal of the user is shaped to follow the contour of a part of the ear canal or concha to be contacted by said each electrode, and
   the ear plug is made of a dimensionally stable material for identical positioning in the ear canal each time it is inserted.

2. The ear plug according to claim 1, wherein the processor is adapted for delivering a signal to the user.

3. The ear plug according to claim 1, wherein the processor is located external to the ear plug.

4. The ear plug according to claim 1, wherein the processor is located inside the ear plug.

5. An ear plug according to claim 1, wherein the connector comprises a conductive wiring drawn in or through said shell of the ear plug.

6. The ear plug according to claim 5, wherein said wiring is arranged to form at least part of one of the electrodes.

7. The ear plug according to claim 1, comprising a rivet extending between at least one of said two electrodes and said connector through at least a part of said shell of said ear plug in such a way that a part of said rivet is arranged flush with said surface of said shell.

8. The ear plug according to claim 7, wherein said part of said rivet is adapted to accommodate said at least one electrode.

9. The ear plug according to claim 1, comprising at least one recess in which at least one of said two electrodes is mounted, a bottom surface of the recess following the contours of the outer surface of the ear plug.

10. The ear plug according to claim 9, wherein the at least one electrode is held in the recess by the at least one electrode comprising at least one of: a close fit between the at least one electrode and the recess, at least one convexity on the at least one electrode corresponding to at least one concavity provided in the recess, and an adhesive.

11. The ear plug according to claim 9, wherein the at least one electrode is made of an electrically conductive flexible material.

12. The ear plug according to claim 1, wherein the electrodes are polarizable electrodes made of a material comprising at least one material selected from the group consisting of stainless steel, platinum-iridium, silver, titanium, platinum and tungsten.

13. The ear plug according to claim 1, wherein the electrodes are non- polarizable electrodes.

14. The ear plug according to claim 1, wherein each of the electrodes covers an area of at least 1 $mm^2$, and no more than 30 $mm^2$.

15. The ear plug according to claim 1, wherein said ear plug is a hearing aid ear plug having a sound presentation component for presenting sound from a hearing aid to said ear canal of said user.

16. The ear plug according to claim 1, wherein said processor is a processor for processing of said brain wave signals to provide information for detecting a medical condition of the user.

17. A hearing aid comprising a microphone, a hearing aid signal processor, and an ear plug for presenting processed sound from said hearing aid signal processor to an ear canal of a user, wherein said ear plug is an ear plug according to claim 1.

18. A method of producing an ear plug according to claim 1, the method comprising the steps of, tracing the shape of a part of at least one of the user's ear canal and concha, converting the traced shape into a digital form, and and building the ear plug based on the digital form by means of a computer controlled production process.

* * * * *